United States Patent
Yalamanchili et al.

(10) Patent No.: US 10,289,756 B2
(45) Date of Patent: May 14, 2019

(54) SYSTEM AND METHOD FOR DESIGNING PIN JOINT

(71) Applicant: Caterpillar Inc., Peoria, IL (US)

(72) Inventors: Vijay K. Yalamanchili, Savoy, IL (US); Yang-Kyoo Chang, Dunlap, IL (US)

(73) Assignee: Caterpillar Inc., Deerfield, IL (US)

( * ) Notice: Subject to any disclaimer, the term of this patent is extended or adjusted under 35 U.S.C. 154(b) by 330 days.

(21) Appl. No.: 15/044,158

(22) Filed: Feb. 16, 2016

(65) Prior Publication Data
US 2017/0235851 A1 Aug. 17, 2017

(51) Int. Cl.
| | |
|---|---|
| *G06F 17/50* | (2006.01) |
| *F16M 11/14* | (2006.01) |
| *F16M 11/18* | (2006.01) |
| *B29C 65/00* | (2006.01) |
| *H01H 3/46* | (2006.01) |
| *B60G 21/05* | (2006.01) |
| *A61B 17/29* | (2006.01) |

(52) U.S. Cl.
CPC ...... *G06F 17/50* (2013.01); *A61B 2017/2939* (2013.01); *B29C 66/8322* (2013.01); *B60G 21/05* (2013.01); *F16M 11/14* (2013.01); *F16M 11/18* (2013.01); *H01H 3/46* (2013.01); *Y10T 403/75* (2015.01)

(58) Field of Classification Search
None
See application file for complete search history.

(56) References Cited

U.S. PATENT DOCUMENTS

| | | | | |
|---|---|---|---|---|
| 4,193,707 | A * | 3/1980 | Doden | B62D 7/18 403/133 |
| 5,769,557 | A * | 6/1998 | Beals | E02F 9/006 403/157 |
| 8,028,258 | B1 * | 9/2011 | Ogami | G06F 17/5068 716/110 |
| 9,879,412 | B2 * | 1/2018 | Miyagawa | E04B 1/1903 |
| 2002/0042703 | A1 * | 4/2002 | Furusu | G09B 23/30 703/11 |
| 2003/0070476 | A1 * | 4/2003 | Heidemann | F16C 11/0647 73/117.02 |
| 2003/0115020 | A1 * | 6/2003 | Adachi | E02F 9/205 702/184 |

(Continued)

*Primary Examiner* — Kibrom K Gebresilassie
(74) *Attorney, Agent, or Firm* — Harrity & Harrity LLP

(57) ABSTRACT

A computer-implemented method for designing a pin joint having a bearing member and a pin member received within the bearing member is provided. The method includes receiving, via a Graphical User Interface (GUI), at least one input related to one or more pin joint configuration parameters. The method includes receiving, via the GUI, at least one input related to one or more pin member design parameters. The method includes receiving, via the GUI, at least one input related to one or more bearing member design parameters. The method includes calculating a set of design parameters of the pin joint based on the inputs related to the pin joint configuration parameters, the pin member design parameters, and the bearing member design parameters. The method includes generating an output design of the pin joint based on the comparison between the calculated set of design parameters with a set of predefined design parameters.

20 Claims, 12 Drawing Sheets

(56) References Cited

U.S. PATENT DOCUMENTS

| | | | | |
|---|---|---|---|---|
| 2004/0006410 | A1* | 1/2004 | Lee | B60G 17/0182 701/1 |
| 2004/0140006 | A1* | 7/2004 | Fuksa | B29C 65/08 137/454.4 |
| 2004/0228676 | A1* | 11/2004 | Oertley | E02F 3/283 403/154 |
| 2005/0162419 | A1* | 7/2005 | Kim | G06T 15/00 345/419 |
| 2005/0223327 | A1* | 10/2005 | Cunningham | G09B 23/30 715/701 |
| 2005/0278665 | A1* | 12/2005 | Gentry | G06F 17/5072 716/139 |
| 2006/0122027 | A1* | 6/2006 | Dalenberg | F16H 57/08 475/338 |
| 2006/0149517 | A1 | 7/2006 | El-Sayed et al. | |
| 2006/0175513 | A1* | 8/2006 | Kuhn | F16C 11/0628 248/371 |
| 2007/0011496 | A1 | 1/2007 | Ahmed et al. | |
| 2010/0209180 | A1* | 8/2010 | Hasselbusch | F16J 15/344 403/150 |
| 2011/0005073 | A1* | 1/2011 | Meisborn | F01L 1/14 29/888.03 |
| 2011/0037488 | A1* | 2/2011 | Shilpiekandula | B82Y 10/00 324/690 |
| 2011/0313720 | A1 | 12/2011 | Li et al. | |
| 2012/0003069 | A1* | 1/2012 | Hagiwara | E02F 9/226 414/685 |
| 2013/0045040 | A1* | 2/2013 | Ginn | B62D 55/0842 403/26 |
| 2013/0054199 | A1 | 2/2013 | Wu et al. | |
| 2014/0261152 | A1* | 9/2014 | Tanaka | E02F 9/2033 116/230 |
| 2015/0154333 | A1* | 6/2015 | Chai | G06F 17/5081 716/112 |
| 2017/0015402 | A1* | 1/2017 | Lakic | B64C 1/26 |
| 2017/0169146 | A1* | 6/2017 | Chen | G06F 17/5022 |
| 2018/0244518 | A1* | 8/2018 | Miraglia | B82B 3/0052 |

\* cited by examiner

FIG. 5

SYSTEM AND METHOD FOR DESIGNING PIN JOINT

TECHNICAL FIELD

The present disclosure generally relates to pin joints of machines, and more particularly, to a system and method for designing a pin joint.

BACKGROUND

Machines such as, an excavator, a mining truck, a dump truck, include various components that have relative rotational movements with respect to each other. Such components, for example, articulated linkages, track assemblies, lift arms, work implements, are coupled by means of pin joints. Typically, a pin joint includes a bearing member and a pin member removably received within the bearing member. The pin joint is designed to withstand high load operating conditions in the machines, because an inaccurate design of the pin joint may cause failures of the components connected through the pin joint. Conventional methods for designing the pin joint may be complex, time consuming. Further, conventional methods for designing or selecting the pin joint may be unreliable, and may consider fewer parameters.

U.S. Patent Publication No. 2013/0054199 is related to a fastening model representation device in a fastener aided design system. The fastening model representation device includes at least one fastener model with an information storage module that stores three-dimensional information of the fastener model. The information storage module stores related information of the fastener model such as a name, an identification number, weight, coordinates and materials of the fastener model. The information storage module can also include at least one of installation standards, connected parts, amendment information, heat treatment, detail parameters and mechanical properties of the fastener model. The related information and the naming information are shared by the fasteners of the same class in a manner of a digital dictionary. The three-dimensional information is stored in a local storage area of the fastener model and may be directly accessed, thereby providing a user with various graphic representations and statistical information of the fastener model.

SUMMARY OF THE DISCLOSURE

One aspect of the present disclosure relates to a computer-implemented method for designing a pin joint having a bearing member and a pin member received within the bearing member. The method includes receiving, via a Graphical User Interface (GUI), at least one input related to one or more pin joint configuration parameters. The method includes receiving, via the GUI, at least one input related to one or more pin member design parameters. The method includes receiving, via the GUI, at least one input related to one or more bearing member design parameters. The method includes calculating a set of design parameters of the pin joint based on the inputs related to the pin joint configuration parameters, the pin member design parameters, and the bearing member design parameters. The method includes generating an output design of the pin joint based on the comparison between the calculated set of design parameters with a set of predefined design parameters.

Another aspect of the present disclosure relates to a system for designing a pin joint having a pin member and a bearing member received within the bearing member. The system includes a Graphical User Interface (GUI) configured to receive one or more inputs. The system includes a pin joint database configured to store a set of predefined design parameters. The system further includes a processing device in communication with the GUI and the pin joint database. The processing device is configured to receive, via the GUI, at least one input related to one or more pin joint configuration parameters. The processing device is configured to receive, via the GUI, at least one input related to one or more pin member design parameters. The processing device is configured to receive, via the GUI, at least one input related to one or more bearing member design parameters. The processing device is configured to calculate a set of design parameters of the pin joint based on the inputs related to the pin joint configuration parameters, the pin member design parameters, and the bearing member design parameters. The processing device is further configured to generate an output design of the pin joint based on the comparison between the calculated set of design parameters with a set of predefined design parameters.

Another aspect of the present disclosure relates to a computer-readable storage device storing instructions for designing a pin joint having a bearing member and a pin member received within the bearing member. The instructions causes a computer to perform operations including receiving, via a Graphical User Interface (GUI), at least one input related to one or more pin joint configuration parameters. The operations include receiving, via the GUI, at least one input related to one or more pin member design parameters. The operations also include receiving, via the GUI, at least one input related to one or more bearing member design parameters. The operations further include calculating a set of design parameters of the pin joint based on the inputs related to the pin joint configuration parameters, the pin member design parameters, and the bearing member design parameters. The operations also include generating an output design of the pin joint based on the comparison between the calculated set of design parameters with a set of predefined design parameters.

Other features and aspects of this disclosure will be apparent from the following description and the accompanying drawings.

BRIEF DESCRIPTION OF THE DRAWINGS

FIG. 5 to FIG. 7 are GUI of the system displaying various process tabs for bearing member design parameters, according to an embodiment of the present disclosure;

DETAILED DESCRIPTION

Reference will now be made in detail to specific embodiments or features, examples of which are illustrated in the accompanying drawings. Wherever possible, corresponding or similar reference numbers will be used throughout the drawings to refer to the same or corresponding parts.

Figure 1:
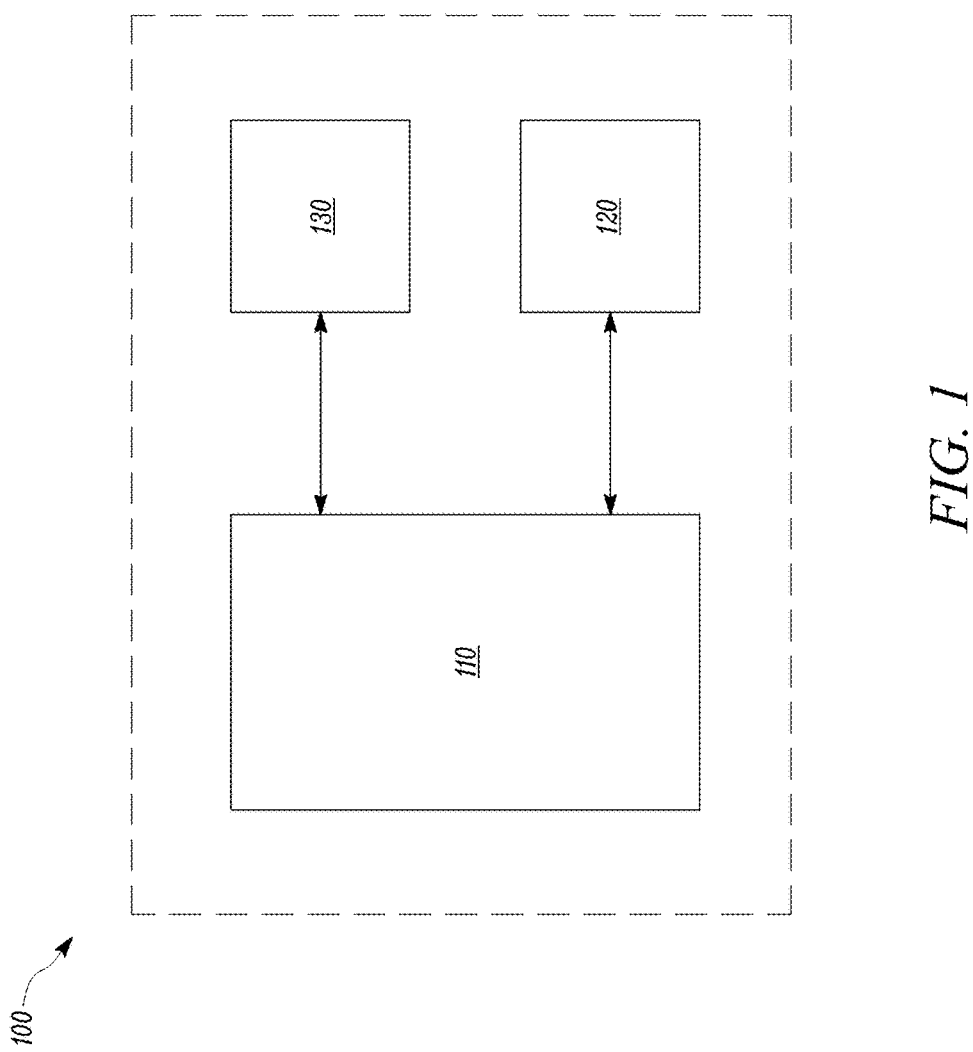
FIG. 1 is a system for designing a pin joint, according to an embodiment of the present disclosure.

FIG. 1 illustrates a block diagram of a system 100, according to an embodiment of the present disclosure. The system 100 may be employed to design a pin joint 102 (shown in FIG. 2). The pin joint 102 may be used to couple two or more components that may have a relative movement with respect to each other. In an example, the pin joint 102 may be used to couple the components, such as articulated linkages, track assemblies, lift arm, work implement or the like, of a machine (not shown). The machine may include a bulldozer, an excavator, a mining truck or any other machine related to various applications such as agriculture, mining, forestry, or the like. The pin joint 102 may include a bearing member 104 and a pin member 106 received within the bearing member 104. The bearing member 104 may define a bore which receives the pin member 106 to rotatably couple two or more components of the machine. Further, the pin joint 102 may be subjected to a high load due to the relative movement of such components therebetween. Therefore, an accurate design of the pin joint 102 may be desired to withstand a high load.

The system 100 includes a Graphical User Interface (GUI) 110, a processing device 120 and a pin joint database 130. The GUI 110 may be configured to receive one or more user inputs. Further, the GUI 110 may be configured to display one or more outputs. In various examples, the GUI 110 may be at least one of a touch based interface, a keyboard based interface, a pointing device (e.g., a mouse) based interface, or a combination thereof.

The processing device 120 may be in communication with each of the GUI 110 and the pin joint database 130. The processing device 120 may be any microprocessor based system, for example, a computer. The processing device 120 may be configured to receive one or more user inputs via the GUI 110. The processing device 120 may also be configured to execute instructions based on the user inputs and provide one or more outputs to the users.

The pin joint database 130 may be configured to store information associated with the pin joint 102. For example, the pin joint database 130 may store a set of predefined design parameters associated with a design of the pin joint 102. The set of predefined design parameters may be indicative of design criteria for design for the pin joint 102. Further, a library having a plurality of pin joint designs of existing pin joints may also be stored in the pin joint database 130. The pin joint database 130 may also store information related to one or more components that may be coupled by the pin joint 102. The pin joint database 130 may also be configured to receive output files from the processing device 120 and store the received files. Further, the processing device 120 may be configured to lookup in the pin joint database 130 and retrieve data from the pin joint database 130. In one embodiment, the pin joint database 130 may be an in-built memory that is integral with the processing device 120. In another embodiment, the pin joint database 130 may be external to the processing device 120.

Referring to FIGS. 2 to 10, the GUI 110 may include multiple graphical control elements. Each of the graphical control elements may allow a user to provide inputs related to various functions such as, but not limited to, selection of one or more features, creation of one or more files, and the like. The processing device 120 may be configured to receive the inputs via one or more of these graphical control elements and accordingly perform tasks. More specifically, the system 100 may be configured to design or select the pin joint based on inputs received via the GUI 110.

Figure 2:
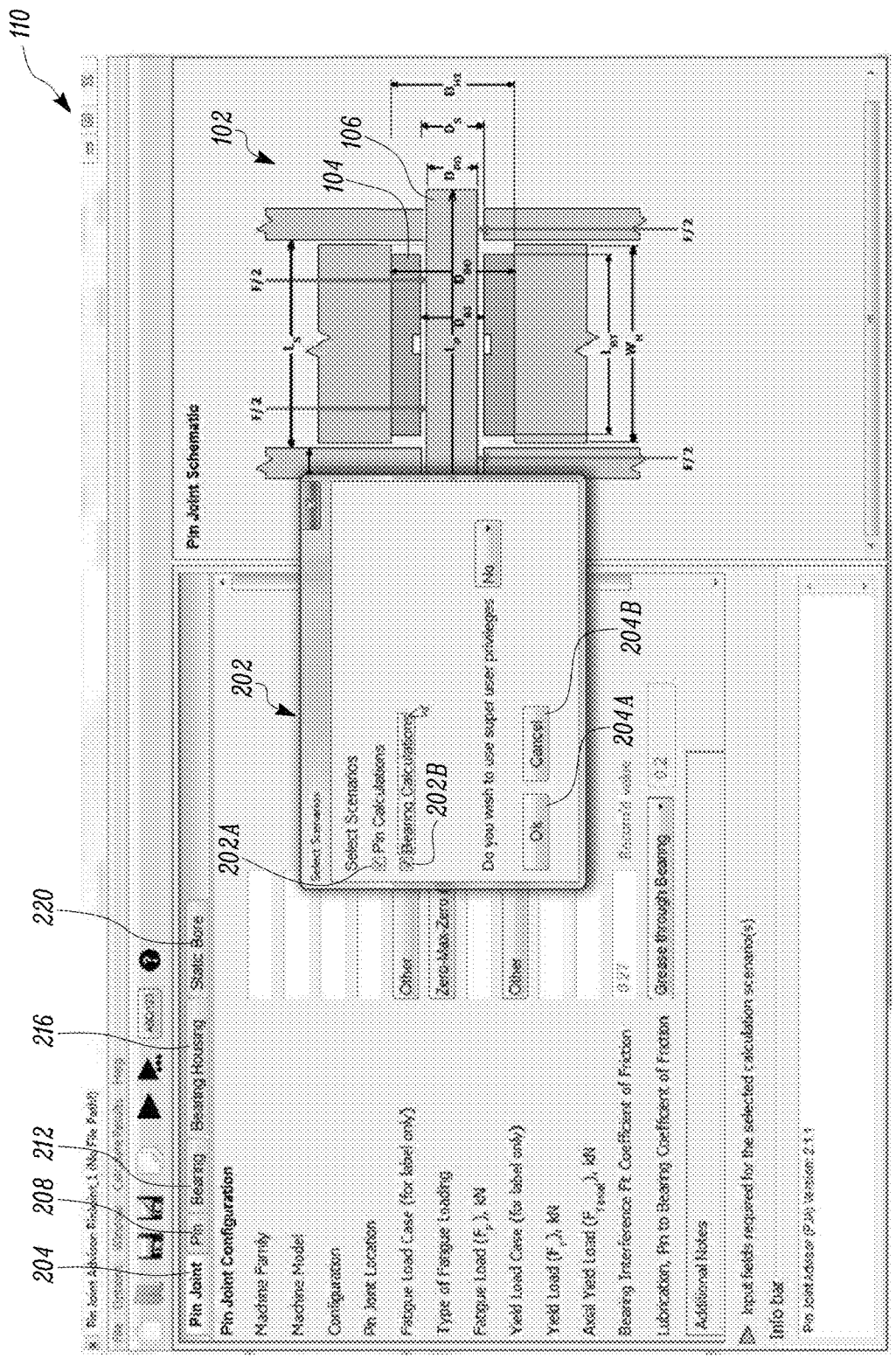
FIG. 2 is a Graphical User Interface (GUI) of the system displaying a process tab for selecting a scenario, according to an embodiment of the present disclosure.

As shown in FIG. 2, the GUI 110 may include a process tab 202 that allows a user to select at least one of a scenario for pin member design and a scenario for bearing member design. The process tab 202A may be, for example, a window, a dialogue box, a page, etc. The process tab 202 also includes control elements 202A, 202B. In the illustrated embodiment, the control elements 202A, 202B are check boxes. Each of the control elements 202A, 202B corresponds to a selection of at least one of a pin calculation associated with the scenario of designing the pin member 106, and a bearing calculation associated with the scenario of designing the bearing member 104, respectively. The process tab 202 further includes control elements 204A, 204B. Upon clicking the control element 204A, the processing device 120 may store the input associated with a selected scenario(s), via the control elements 202A, 202B and may subsequently display or navigate to a process tab 206 (shown in FIG. 3) of the GUI 110. In various embodiments, the process tab 206 may be a window, a dialogue box, a page, etc. Alternatively, a navigation button 204 of the GUI 110 may be used to navigate to the process tab 206.

Figure 3:
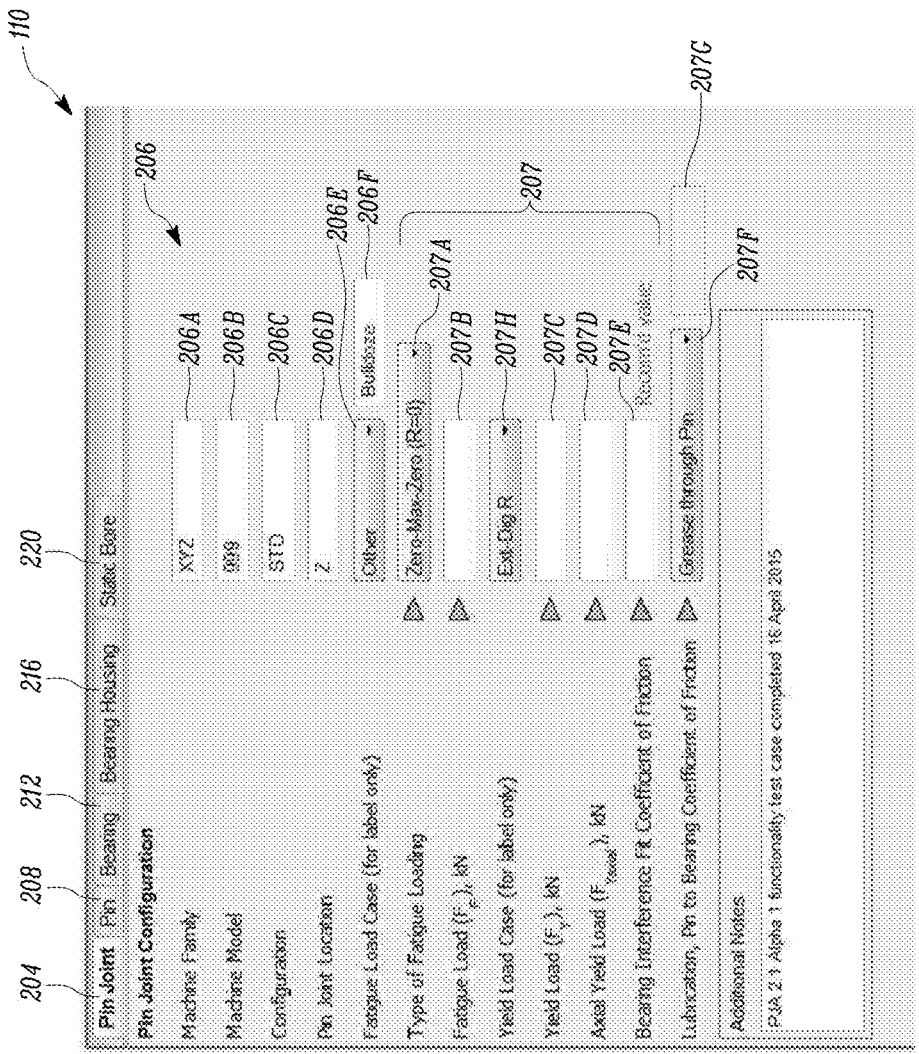
FIG. 3 is a GUI of the system displaying a process tab for pin joint configuration parameters, according to an embodiment of the present disclosure.

Referring to FIG. 3, the process tab 206 includes control elements 206A, 206B, 206C, and 206D. The control element 206A, 206B, 206C and 206D may allow the user to input pin joint details such as, a machine family, a machine model, a configuration, a pin joint location, respectively. The control elements 206AB, 206B, 206C and 206D may be input boxes, drop-down menus, list boxes and the like. The process tab 206 also includes control elements 206E, 206F that may allow the user to provide inputs corresponding to a fatigue load case. The control element 206E may be a drop-down menu or a list box that includes list of fatigue load cases. Further, the control element 206F may be an input box that allows the user to provide information related to the selected fatigue load case.

The process tab 206 further includes a set of control elements 207 that allows the user to provide inputs related to one or more pin joint configuration parameters. In an embodiment, the pin joint configuration parameters include a loading condition of the pin joint 104 and a coefficient of friction between the pin member 106 and the bearing member 104. The set of control elements 207 includes control elements 207A, 207B, 207C, and 207D that may allow the user to provide inputs related to the loading condition of the pin joint 102. In particular, the control elements 207A, 207B, 207C, and 207D allow the user to provide inputs related to a type of fatigue loading, a fatigue load, a yield load, and an axial yield load, respectively. The set of control elements 207 also includes a drop down menu 207H that allows the user to select a yield load case.

Figure 4:
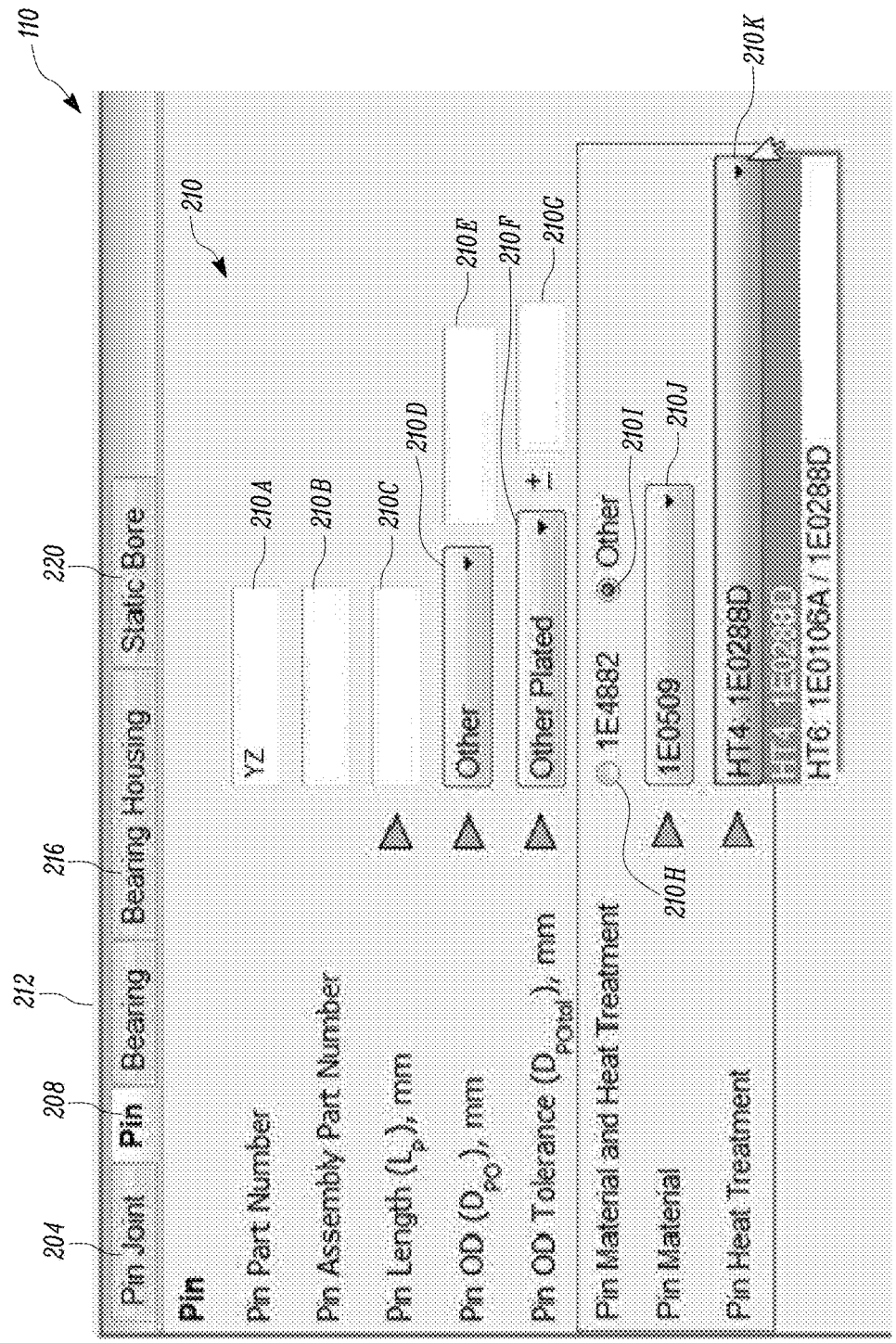
FIG. 4 is a GUI of the system displaying a process tab for pin member design parameters, according to an embodiment of the present disclosure.

The set of control elements 207 further includes a control element 207E. In the illustrated embodiment, the control element 207E is an input box that allows user to provide input related to a bearing interference fit coefficient of friction. Further, the set of control elements 207 includes control elements 207F, 207G. The control elements 207E, 207F, 207G allows the user to provide input related to a coefficient of friction between the pin member 106 and the bearing member 104. In the illustrated embodiment, the control element 207F is a drop down menu that allows the user to select a type of lubrication between the pin member 106 and the bearing member 104. In particular, the processing device 120 may be configured to receive the selection of type of lubrication via the control element 207F. Subsequently, the processing device 120 may also be configured to lookup the pin joint database 130 and retrieve a value of pin to bearing coefficient of friction from the database 130. Further, the processing device 120 may also auto-fill the retrieved value via the control elements 207D for display to the user on the GUI 110. It should be noted that the process tab 206 may include other control elements to allow the user to provide inputs related to various design variables associated with the pin joint 102. Also, one or more control elements may also be deleted from the process tab 206 based on requirements The GUI 100 includes a control element 208 that may be a navigation button. Referring to FIG. 4, the processing device 120 may display or navigate to a process tab 210 on the GUI 110 as the user clicks on the navigation button 208. The process tab 210 may allow the user to provide at least one input related to one or more pin member design parameters. In an embodiment, the pin member design parameters may include a dimensional specification of the pin member 106, a material specification of the pin member 106, and a heat treatment specification of the pin member 106.

The process tab 210 may include control elements 210A, 210B. The control elements 210A, 210B allow the user to provide input related to a pin part number and a pin assembly part number. The processing device 120 may be configured to receive the inputs via the control elements 210A, 210B and retrieve data associated with the pin part number and the pin assembly part number.

The process tab 210 may also include control elements 210C, 210D, 210E, 210F, 210G. The control elements 210C, 210D, 210E, 210F, 210G may allow the user to provide inputs related to the dimensional specification of the pin member. In the illustrated embodiment, the control elements 210C, 210D, 210E, 210F, 210G allow the user to provide inputs related to a pin length, a pin outer diameter, and a pin outer diameter tolerance of the pin member 106. More specifically, the control element 210C is an input box that allows user to provide input related to the pin length of the pin member 106. The control elements 210D, 210E allows the user to provide input related to the pin outer diameter of the pin member 106. The control element 210D is a drop down menu that allows the user to select a value of the pin outer diameter of existing pin joints. Alternatively, the user may also provide a value of pin outer diameter via the control element 210E which may be an input box. Further, the control element 210F is a drop down menu that allows the user to select a type of coating on the pin member 106. The processing device 120 may be configured to receive the selected type of coating and retrieve a value of the pin outer diameter tolerance from the pin joint database 130. Alternatively, the processing device 120 may receive a value of the pin outer diameter tolerance via the control element 210G which is an input box.

Figure 5:
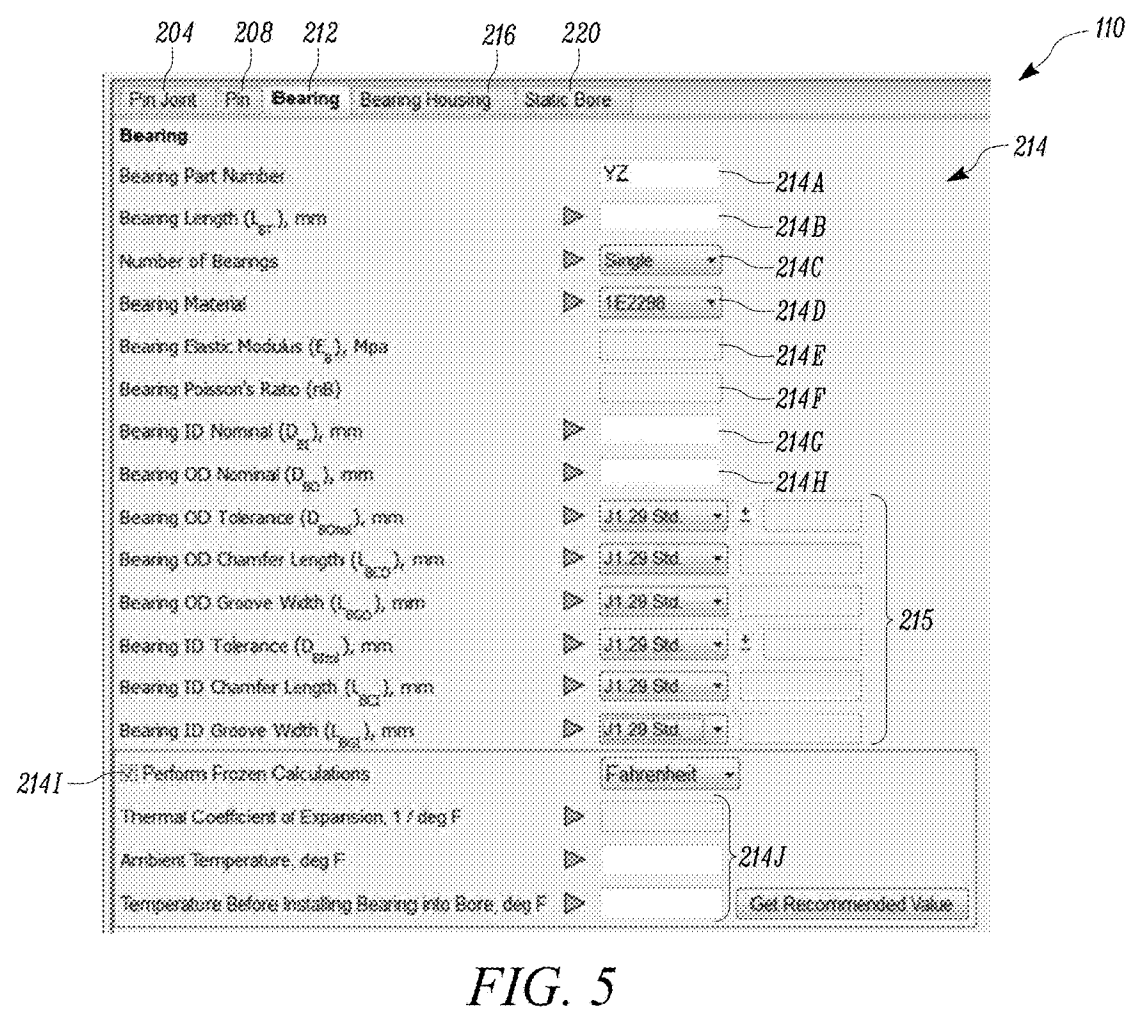

The process tab 210 may further include control elements 210H, 210I that allows user to provide inputs related to the material specification of the pin member 106, and the heat treatment specification of the pin member 106. In the illustrated embodiment, the control elements 210H, 210I are radio buttons that allow user to select one of an existing pin specification or user desired pin specifications. Upon selecting the control element 210H, the processing device 120 may retrieve the heat treatment specifications and the material specifications for further processing. Moreover, upon selecting the control element 210I, the processing device 120 may allow the user to provide user desired pin specification i.e. heat treatment specification and the material specification, via control elements 210J, 210K. It should be noted that the process tab 210 may include other control elements to allow the user to provide inputs related to various design variables associated with the pin member 106. Also, one or more control elements may also be deleted from the process tab 210 based on requirements The GUI 110 includes navigation buttons 212, 216, 220 that may allow the user to provide inputs related to one or more bearing member design parameters. In an embodiment, the bearing member design parameters may include a dimensional specification of the bearing member 104, and a material specification of the bearing member 104. Referring to FIG. 5, the processing device 120 may display or navigate to a process tab 214 on the GUI 110 as the user clicks on the navigation button 212. The process tab 214 includes a control element 214A that may allow user to provide input related to a bearing part number. The process tab 214 also includes a control element 214D that may allow the user to provide input related to the material specification of the bearing member. In the illustrated embodiment, the control element 214D is a drop down menu that allows user to select a type of material of the bearing member 104. Based on the selected type of bearing member, the processing device 120 may be configured to lookup the pin joint database 130 and retrieve information such as, elastic modulus, a Poisson's ratio and the like from the pin joint database 130. Subsequently, the processing device 120 may auto-fill the retrieved information for display to the user on the GUI 110, via control elements 214E, 214F. Alternatively, the control elements 214E, 214F may allow the user to input elastic modulus, Poisson's ratio and utilize the inputs received from the control elements 214E, 214F for further processing. It should be noted that the process tab 214 may include other control elements to allow the user to provide inputs related to various design variables associated with the bearing member 104. Also, one or more control elements may also be deleted from the process tab 206 based on requirements The process tab 214 also includes control elements 214B, 214C that allow the user to provide inputs related to a bearing length, a number of bearing members, respectively. In the illustrated embodiment, the control elements 214B, 214C are input boxes. Further, the process tab 214 may include control elements 214G. The control elements 214 allow user to provide inputs related to information associated with internal diameter of the bearing member. The process tab 212 may also include control elements 214H that may allow the user to provide inputs related to outer diameter of the bearing member 104. Further, the process tab 214 also includes a set of control elements 215 that may allow the user to provide inputs related to variables associated with various dimensional specifications. In an example, the variables may include, but is not limited to, a bearing outer diameter tolerance, a bearing outer diameter chamfer length, a bearing outer diameter groove width, a bearing inner diameter tolerance, a bearing inner diameter chamfer length, a bearing inner diameter groove width. More specifically, the processing device 120 may be configured to receive dimensional specification of the bearing member 104, via the control elements 214B, 214C, 214G, 214H and the set of control elements 215.

Further, a control element 214I of the GUI 110 may allow the user to give an instruction to perform frozen calculations associated with the design of pin joint. The control element 214I may be a radio button or a check box. Upon selecting the control element 214I, the processing device 120 may receive instruction to perform frozen calculation and subsequently, allow the user to provide thermal parameters associated with the frozen calculations, via control elements 214J. In an embodiment, the thermal parameters may include a thermal coefficient of expansion, an ambient temperature, and a temperature before installation of the bearing member 104.

Figure 6:
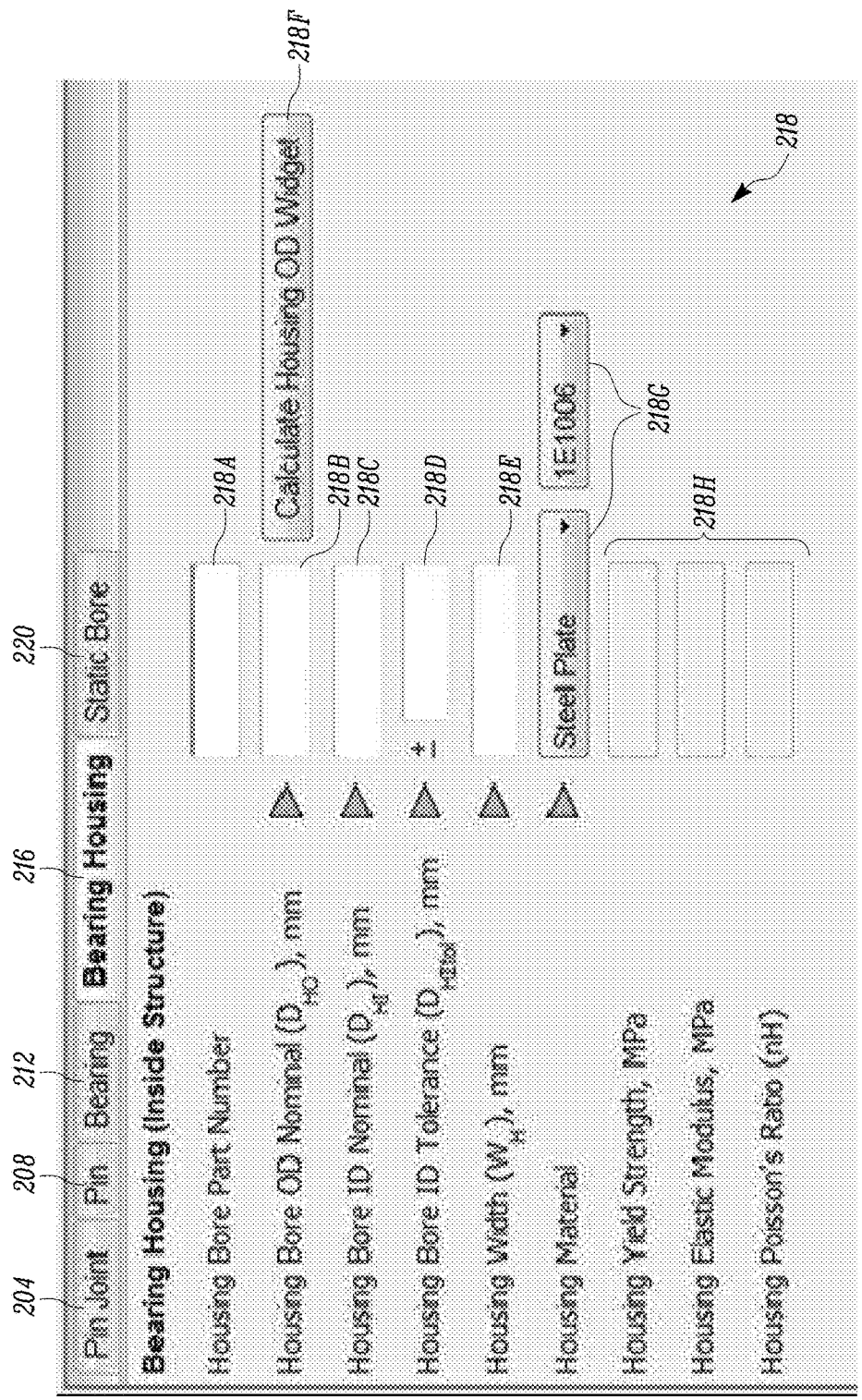
Figure 7:
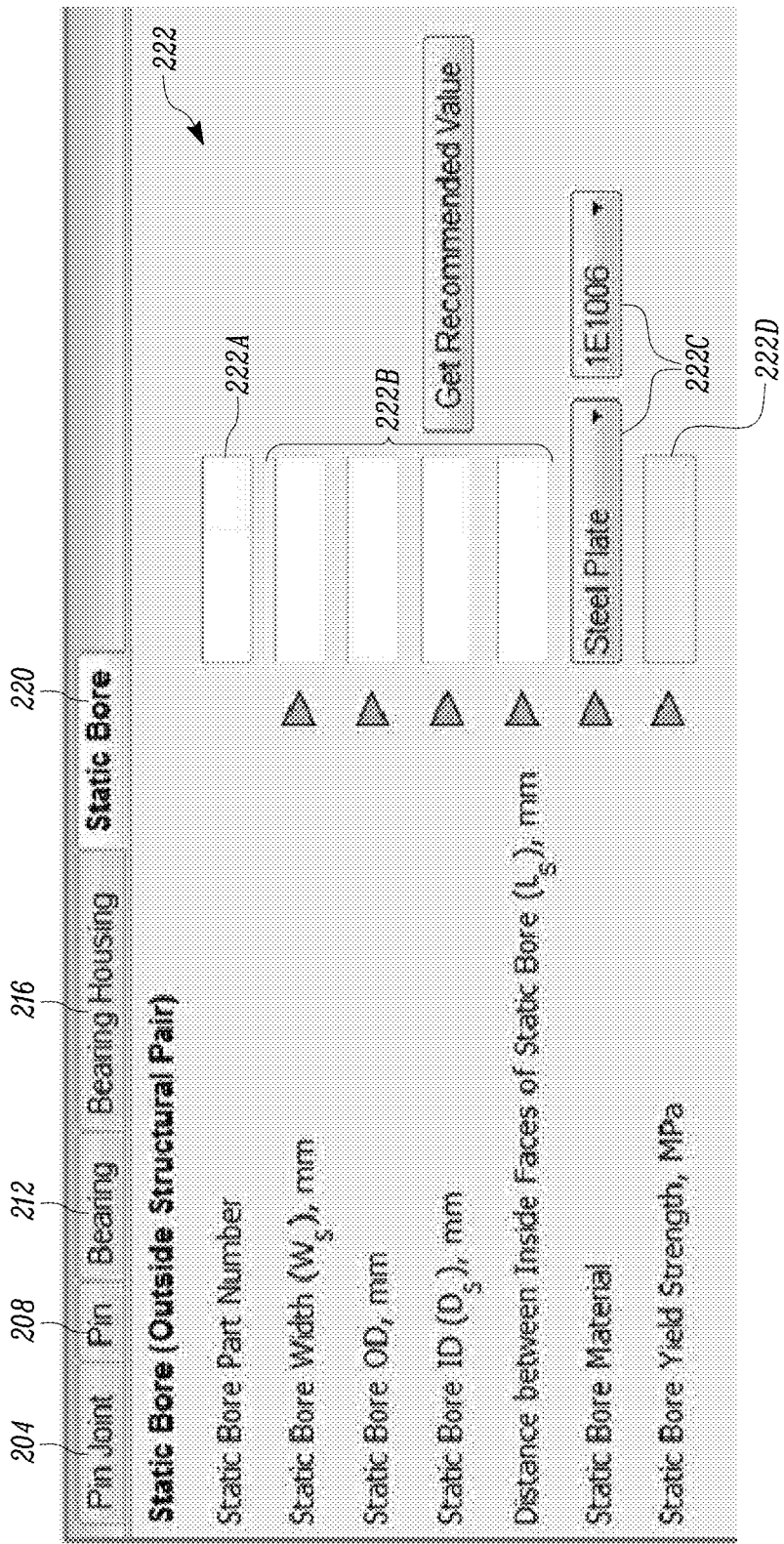

Referring to FIG. 6, the processing device 120 may display or navigate to a process tab 218 on the GUI 110, as the user clicks on the navigation button 216. The process tab 218 allows the user to provide inputs related to one or more design parameters associated with a housing (not shown) of the bearing member 104. In an example, the bearing housing design parameters may include, but not limited to, a housing bore nominal outer diameter, a housing bore inner diameter, a housing bore inner diameter and a housing material. In the illustrated embodiment, the process tab 218 includes a control element 218A that allows the user to provide an input related to housing bore part number. The process tab 218 also includes control elements 218B, 218C, 218D, 218E that allow the user to provide inputs related to a dimensional specification of the housing. In particular, the control elements 218B, 218C, 218D, 218E are input boxes that allow the user to provide inputs related to the housing bore nominal outer diameter, the housing bore inner diameter, the housing bore inner diameter and the housing material. The process tab 218 may also a button 218F. Upon clicking on the button 218F, the processing device 120 may calculate a widget outer diameter of the housing for further processing.

Further, the process tab 218 includes control elements 218G, 218H that may allow the user to provide at least one input related to a material specification of the housing. Moreover, the processing device 120 may be configured to select the a material of the housing upon receiving the input via the control elements 218G, 218H and retrieve mechanical properties associated with the selected material from the pin joint database 130. Subsequently, the processing device 120 may also be configured to display mechanical properties, such as Yield strength, Elastic Modulus etc., via control elements 218H. It should be noted that the process tab 218 may include other control elements to allow the user to provide inputs related to various design variables associated with the housing of the bearing member 104. Also, one or more control elements may also be deleted from the process tab 206 based on requirements Referring to FIG. 7, the processing device 120 may display or navigate to a process tab 222 of the GUI 110 as the user clicks on the navigation button 220. The process tab 222 allows the user to provide inputs related to a dimensional specification and a material specification of a static bore of the bearing member 104. The process tab 222 may include a control element 222A that may allow the user to provide input related to a static bore part member. The process tab 218 may also include control elements 222B that may allow the user to provide inputs related to the dimensional specification of the static bore. In an example, the dimensional specification of the static bore may include, but not limited to, a static bore width, a static bore outer diameter, a static bore inner diameter and a distance between inside faces of the static bore.

Figure 8:
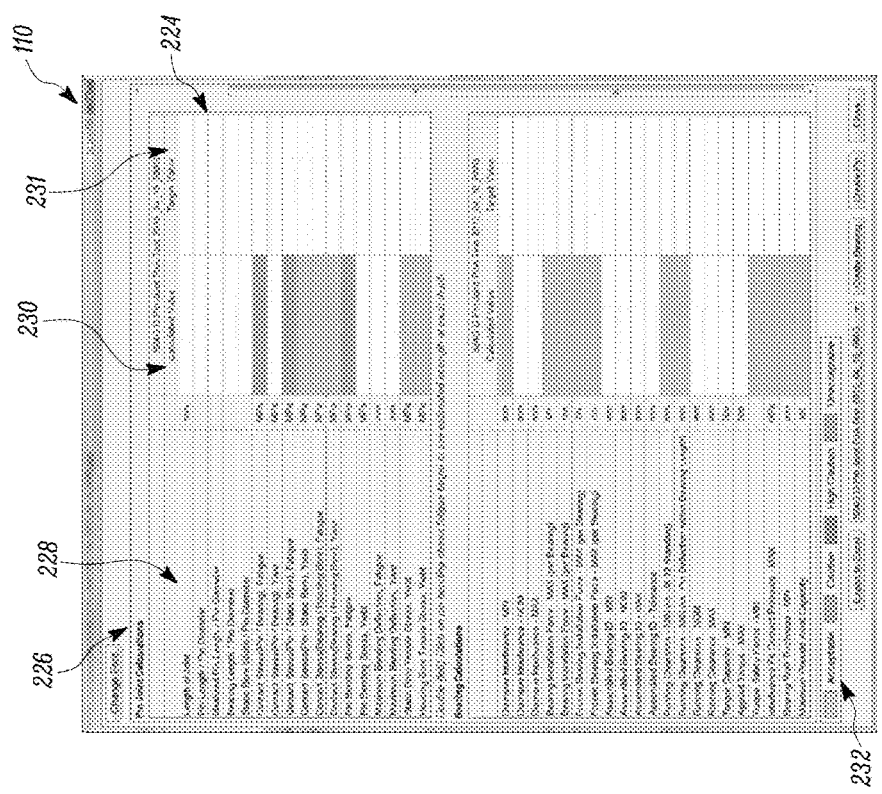
FIG. 8 is a GUI of the system displaying a process tab for displaying a set of design parameters, according to an embodiment of the present disclosure.

The process tab 218 may also include control elements 222C that may allow the user to provide inputs related to t a type of material of the static bore. The processing device 120 may be configured to receive the selection of type of material via the control elements 222C. Subsequently, the processing device 120 may also be configured to lookup the pin joint database 130 and retrieve a value of static bore yield strength from the pin joint database 130. The processing device 120 may further auto-fill the retrieved value in the control elements 207D for display to the user on the GUI 110. It should be noted that the process tab 222 may include other control elements to allow the user to provide inputs related to various design variables associated with the static bore of the bearing member 104. Also, one or more control elements may also be deleted from the process tab 206 based on requirements Referring to FIG. 8, the processing device 120 may be configured to calculate a set of design parameters based on the pin joint configuration parameters, the pin member design parameters, and the bearing member design parameters received via one or more of the process tabs 206, 210, 214, 218 and 224. In an example, the processing device 120 may be configured to perform a fatigue analysis to calculate the set of design parameters. As shown in FIG. 8, the GUI 110 includes a process tab 224 that displays the calculated set of design parameters of the pin joint 102. The process tab 224 includes a table 226 representing the calculated set of design parameters associated with the pin joint 102 in a first column 228. Further, the processing device 120 may be configured to auto-fill the values of the calculated set of design parameters in a second column 230 of the table 226 for display to the user. The processing device 120 may also display a target value of one or more design parameters of the calculated set of parameters in a third column 231.

Subsequently, i.e. after determining the calculated set of design parameters, the processing device 120 may be configured to retrieve the set of predefined parameters from the pin joint database 130 and compare a design parameter of the set of design parameters with a corresponding predefined design parameter. Design criteria for the pin joint 102 may be defined based on the comparison between the calculated set of design parameters and the set of predefined parameters. The processing device 120 may also be configured to generate a warning signal if a design parameter of the set of design parameters does not comply with a corresponding predefined design parameter. In an embodiment, the warning signal may be multiple color markings 232 in the table 226. In various embodiments, the warning signal may also include, but is not limited to, a dialogue box, an audio signal etc. Further, each of the color markings 232 may be suggestive of a level of acceptance of a design of the pin joint 102 with respect to the predefined design parameters. In an example, each of the color markings 232 may be defined based on a safety factor associated with an application of the pin joint.

Figure 9:
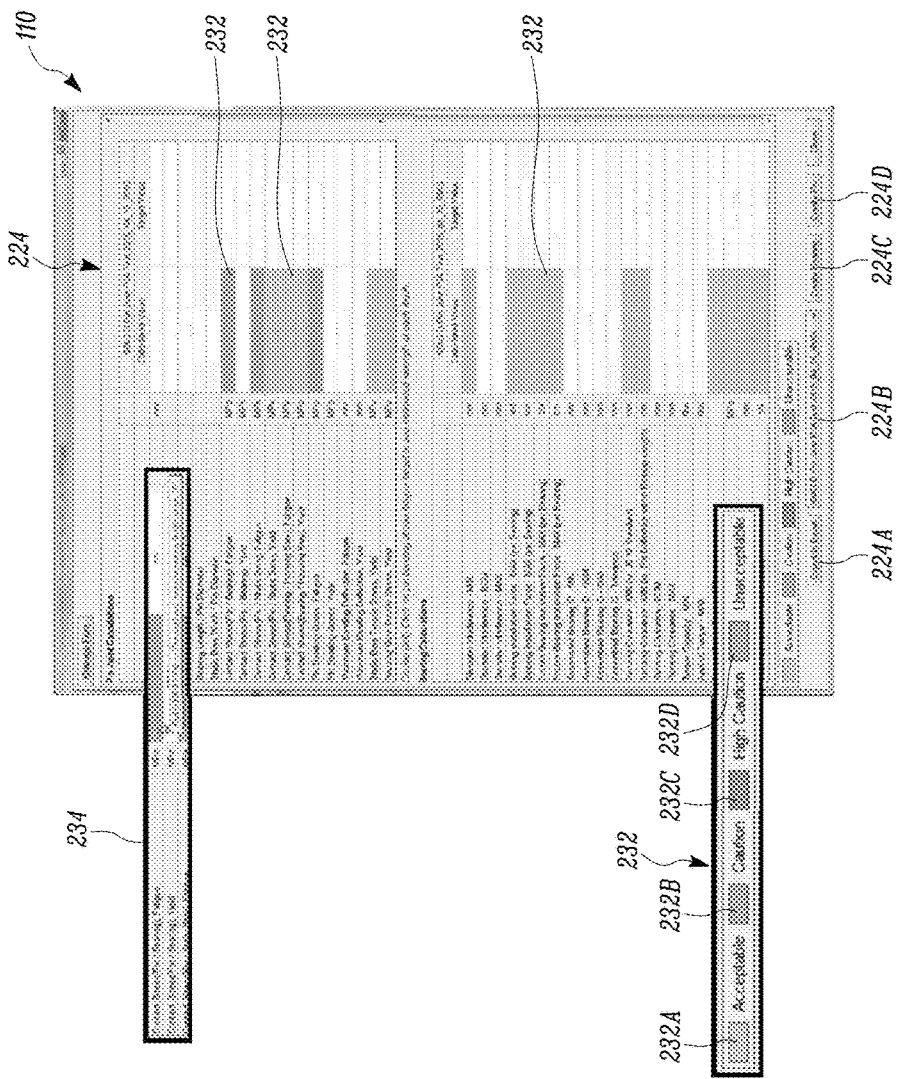
FIG. 9 is a GUI of the system displaying a process tab for suggesting a change in one or more design parameter of the set of design parameters, according to an embodiment of the present disclosure.

Referring to FIG. 9, the color markings 232 include a first marking 232A, a second color marking 232B, a third color marking 232C, and a fourth color marking 232D. The first color marking 232A may indicate a calculated design parameter as "acceptable". The second color marking 232B may indicate a calculated design parameter as "caution". The third color marking 232C may indicate a calculated design parameter as "high caution". The fourth color marking 232D may indicate a calculated design parameter as "unacceptable". The processing device 120 may be configured to suggest a change in one or more design parameters of the set of design parameters, via the GUI 110 as illustrated in FIG. 9. The suggestion on change in one or more design parameters of the set of design parameters may be based on the comparison between the calculated set of design parameters with the set of predefined design parameters. In particular, as the user clicks the color markings 232 of the process tab 224, the processing device 120 may display a dialogue box 234 suggesting a change in a value of a design parameter if the design parameter does not match a corresponding predefined design parameter. As shown in FIG. 9, the process tab 224 also includes control elements 224A, 224B. In the illustrated embodiment, the control element 224A is a button and the control element 224B is a drop down menu. The control element 224A allows the user to save the calculated set of design parameters in spreadsheet format.

Further, the processing device 120 may also be configured to generate an output design of the pin joint 102, via the GUI 110, based on the comparison between the calculated set of design parameters and the set of predefined design parameters. In an example, the processing device 120 is configured to generate an output design for each of the pin member 106 of the pin joint 102 and the bearing member 104 of the pin joint 102, individually. In particular, the process tab 224 of the GUI 110 includes control elements 224C, 224D that allow user to provide inputs pertaining to generation of output design. Upon clicking the control element 224C of the process tab 224, the processing device 120 may receive instructions to generate the output design of the pin member 106. Similarly, upon clicking the control element 224D of the process tab 224, the processing device 120 may receive instructions to generate the output design of the bearing member 104. Moreover, upon receiving instructions via at least one of the control elements 224C, 224D, the processing device 120 may display or navigate to a process tab 236 (shown in FIG. 10) of the GUI 110.

Figure 10:
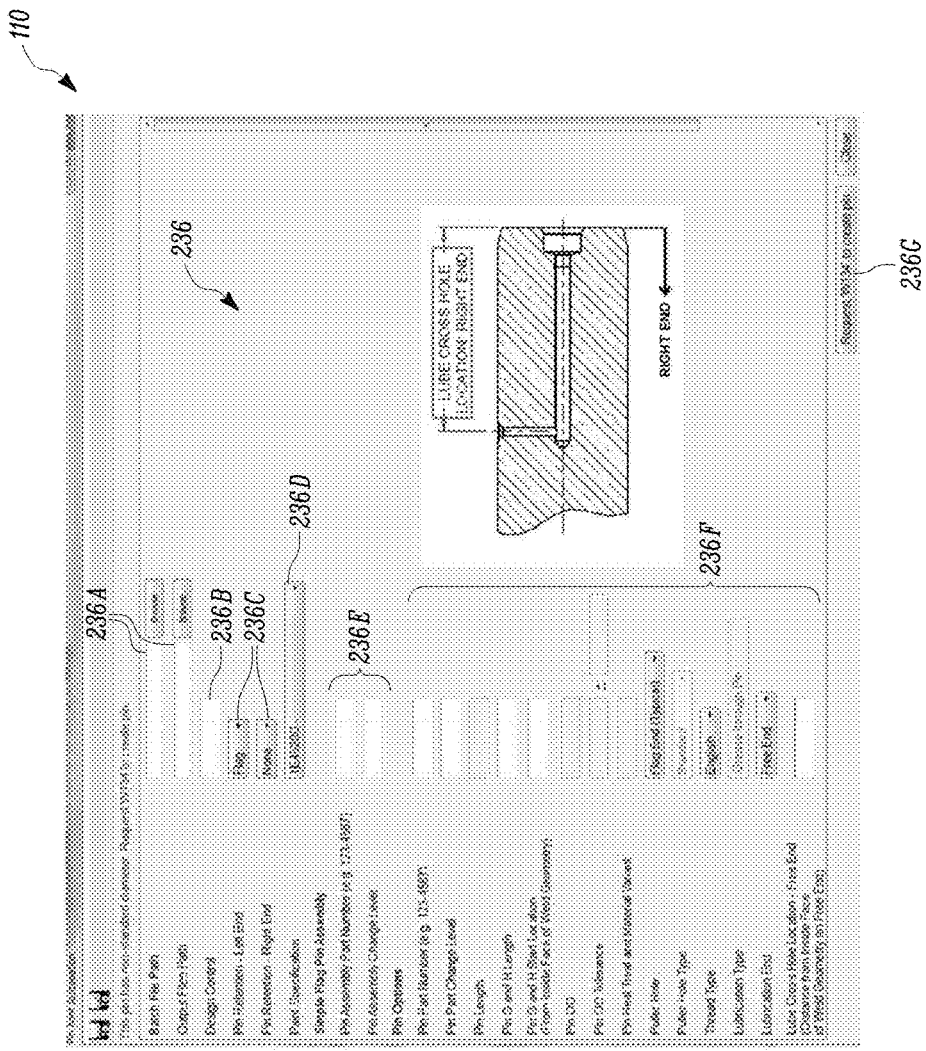
FIG. 10 is a GUI of the system displaying a process tab for selecting an output parameter, according to an embodiment of the present disclosure.

Referring to FIG. 10, the process tab 236 of the GUI 110 allows the user to provide inputs indicative of one or more output parameters. In an embodiment, the output parameters include, but not limited to, file path, a design control, a pin retention, a paint specification, simple flag pin assembly parameters, and multiple pin options. In the illustrated embodiment, the process tab 236 includes control elements 236A that may allow user to provide inputs related to the file path. The process tab 236 also includes control elements 236B, 236C, 236D that may allow the user to provide inputs related to the design control, the pin retention, and the paint specification, respectively. The process tab 236 further includes control elements 236E, 236F that allow the user to provide inputs related to simple flag pin assembly parameters, and pin options, respectively.

Further, upon clicking a control element 236G of the process tab 236, the processing device 120 may be configured to generate the output design of the pin joint 102 based on the set of design parameters and the output parameters. In various examples, the processing device 120 may generate the output design of the pin joint 102 in various formats such as an excel spreadsheet, a 2D model, a 3D model, etc. Further, the processing device 120 may also be configured to compare the output design of the pin joint 102 with a plurality of pin joint designs already stored in the library of existing pin joints. The processing device 120 may also suggest a pin joint from the library of existing pin joints based on comparison between the output design and the plurality of pin joint designs of the library of existing pin joints. For example, if a pin joint of existing pin joints has the calculated set of design parameters, the processing device 120 may generate the output design similar to the pin joint of existing pin joints.

A person of ordinary skill in the art will acknowledge that the GUI 110 and the corresponding graphical control elements explained above are merely exemplary in nature and hence non-limiting of this disclosure. Moreover, necessary design and/or functional modifications may be possible for the GUI 110 without deviating from the scope of the present disclosure. Additional control elements may also be included in the GUI 110 and one or more control elements may also be deleted from the GUI 110 based on requirements. Also, Arrangements and/or rearrangements of the control elements within the GUI 110 is within the scope of the present disclosure.

Figure 11:
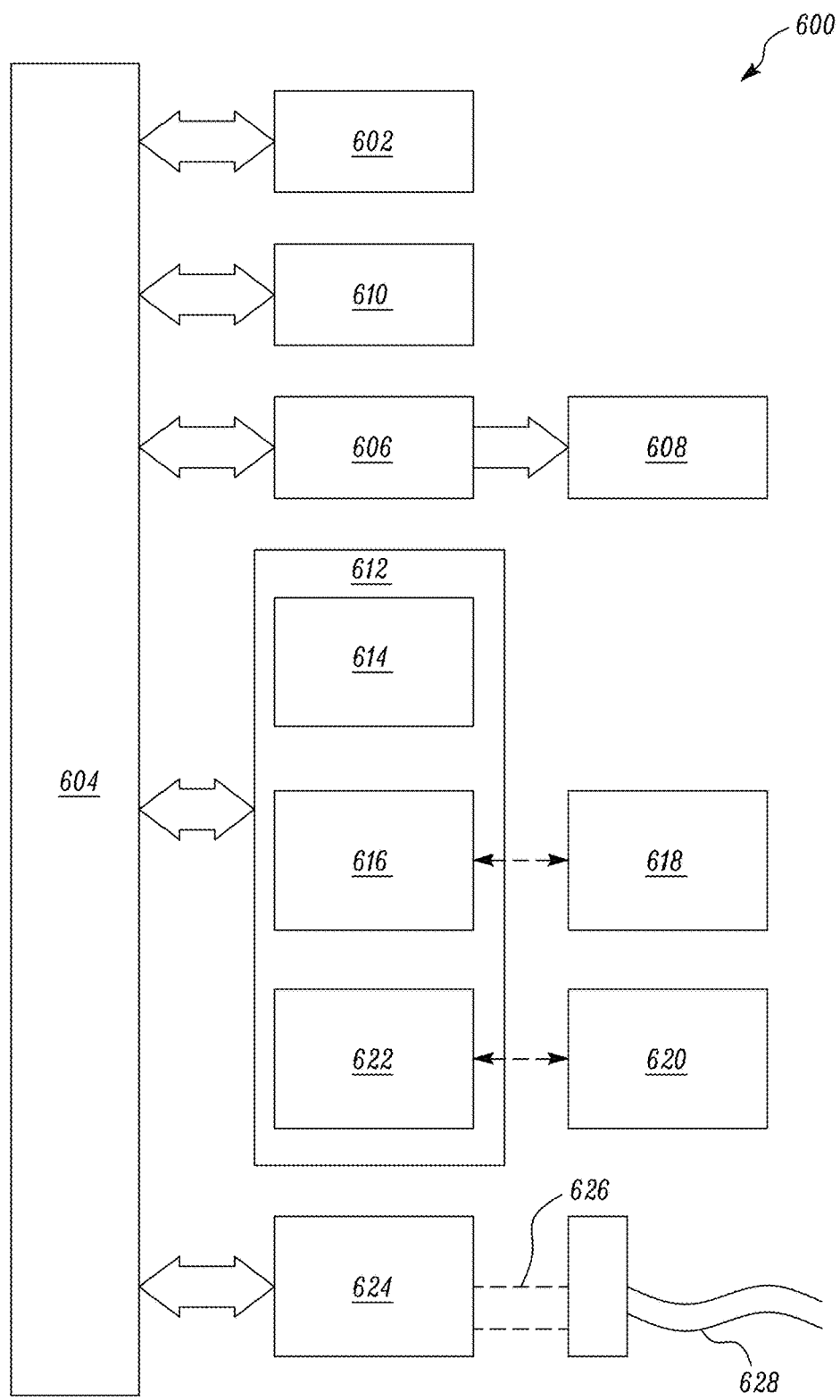
FIG. 11 is a block diagram of an exemplary computer based system, according to an embodiment of the present disclosure.

In fact, in accordance with an embodiment of the present disclosure, the present disclosure is directed towards one or more computer systems capable of carrying out the functionality described herein. An example of the computer based system includes a computer based system 600, which is shown by way of a block diagram in FIG. 11.

The computer based system 600 includes at least one processor, such as a processor 602. The processor 602 may be connected to a communication infrastructure 604, for example, a communications bus, a cross-over bar, a network, and the like. Various software embodiments are described in terms of this exemplary computer based system 600. Upon perusal of the present description, it will become apparent to a person skilled in the relevant art(s) how to implement the present disclosure using other computer systems and/or architectures.

The computer based system 600 includes a display interface 606 that forwards graphics, text, and other data from the communication infrastructure 604, or from a frame buffer (not shown) for display on a display unit 608.

The computer based system 600 further includes a main memory 610, such as random access memory (RAM), and may also include a secondary memory 612. The secondary memory 612 may further include, for example, a hard disk drive 614 or a removable storage drive 616, representing a floppy disk drive, a magnetic tape drive, an optical disk drive, etc. The removable storage drive 616 reads from and/or writes to a removable storage unit 618 in a well known manner. The removable storage unit 618 may represent a floppy disk, magnetic tape or an optical disk, and may be read by and written to by the removable storage drive 616. As will be appreciated, the removable storage unit 618 includes a computer usable storage medium having stored therein, computer software and/or data.

In accordance with various embodiments of the present disclosure, the secondary memory 612 may include other similar devices for allowing computer programs or other instructions to be loaded into the computer based system 600. Such devices may include, for example, a removable storage unit 620, and an interface 622. Examples of such may include a program cartridge and cartridge interface (such as that found in video game devices), a removable memory chip (such as, an erasable programmable read only memory (EPROM), or programmable read only memory (PROM)) and associated socket, and other removable storage units and interfaces, which allow software and data to be transferred from the removable storage unit 620 to the computer based system 600.

The computer based system 600 may further include a communication interface 624. The communication interface 624 allows software and data to be transferred between the computer based system 600 and external devices. Examples of the communication interface 624 include, but may not be limited to a modem, a network interface (such as an Ethernet card), a communications port, a Personal Computer Memory Card International Association (PCMCIA) slot and card, and the like. Software and data transferred via the communication interface 624 may be in the form of a plurality of signals, hereinafter referred to as signals 626, which may be electronic, electromagnetic, optical or other signals capable of being received by the communication interface 624. The signals 626 may be provided to the communication interface 624 via a communication path (e.g., channel) 628. The communication path 628 carries the signals 626 and may be implemented using wire or cable, fiber optics, a telephone line, a cellular link, a radio frequency (RF) link and other communication channels.

In this document, the terms "computer-readable storage device" are used to generally refer to media such as the removable storage drive 616, a hard disk installed in the hard disk drive 614, the signals 626, a floppy disk (not shown), and the like. These computer-readable storage device provide software to the computer based system 600. The present disclosure is directed to such computer-readable storage devices.

Computer programs (also referred to as computer control logic) may be stored in the main memory 610 and/or the secondary memory 612. The computer programs may also be received from the computer-readable storage device via the communication infrastructure 604. Such computer programs, when executed, enable the computer based system 600 to perform the functions consistent with the present disclosure, as discussed herein. In particular, the computer programs, when executed, enable the processor 602 to perform the features of the present disclosure. Accordingly, such computer programs represent controllers of the computer based system 600.

In accordance with an embodiment of the present disclosure, where the disclosure is implemented using a software, the software may be stored in a computer-readable storage device and loaded into the computer based system 600 using the removable storage drive 616, the hard disk drive 614 or the communication interface 624. The control logic (software), when executed by the processor 602, causes the processor 602 to perform the functions of the present disclosure as described herein.

In another embodiment, the present disclosure is implemented primarily in hardware using, for example, hardware components, such as, application specific integrated circuits (ASIC). Implementation of the hardware state machine so as to perform the functions described herein will be apparent to persons skilled in the relevant art(s). In yet another embodiment, the present disclosure is implemented using a combination of both the hardware and the software.

Various embodiments disclosed herein are to be taken in the illustrative and explanatory sense, and should in no way be construed as limiting of the present disclosure. All numerical terms, such as, but not limited to, "first" and "second" or any other ordinary and/or numerical terms, should also be taken only as identifiers, to assist the reader's understanding of the various embodiments, variations, components, and/or modifications of the present disclosure, and may not create any limitations, particularly as to the order, or preference, of any embodiment, variation, component and/or modification relative to, or over, another embodiment, variation, component and/or modification.

It is to be understood that individual features shown or described for one embodiment may be combined with individual features shown or described for another embodiment. The above described implementation does not in any way limit the scope of the present disclosure. Therefore, it is to be understood although some features are shown or described to illustrate the use of the present disclosure in the context of functional segments, such features may be omitted from the scope of the present disclosure without departing from the spirit of the present disclosure as defined in the appended claims.

INDUSTRIAL APPLICABILITY

Figure 12:
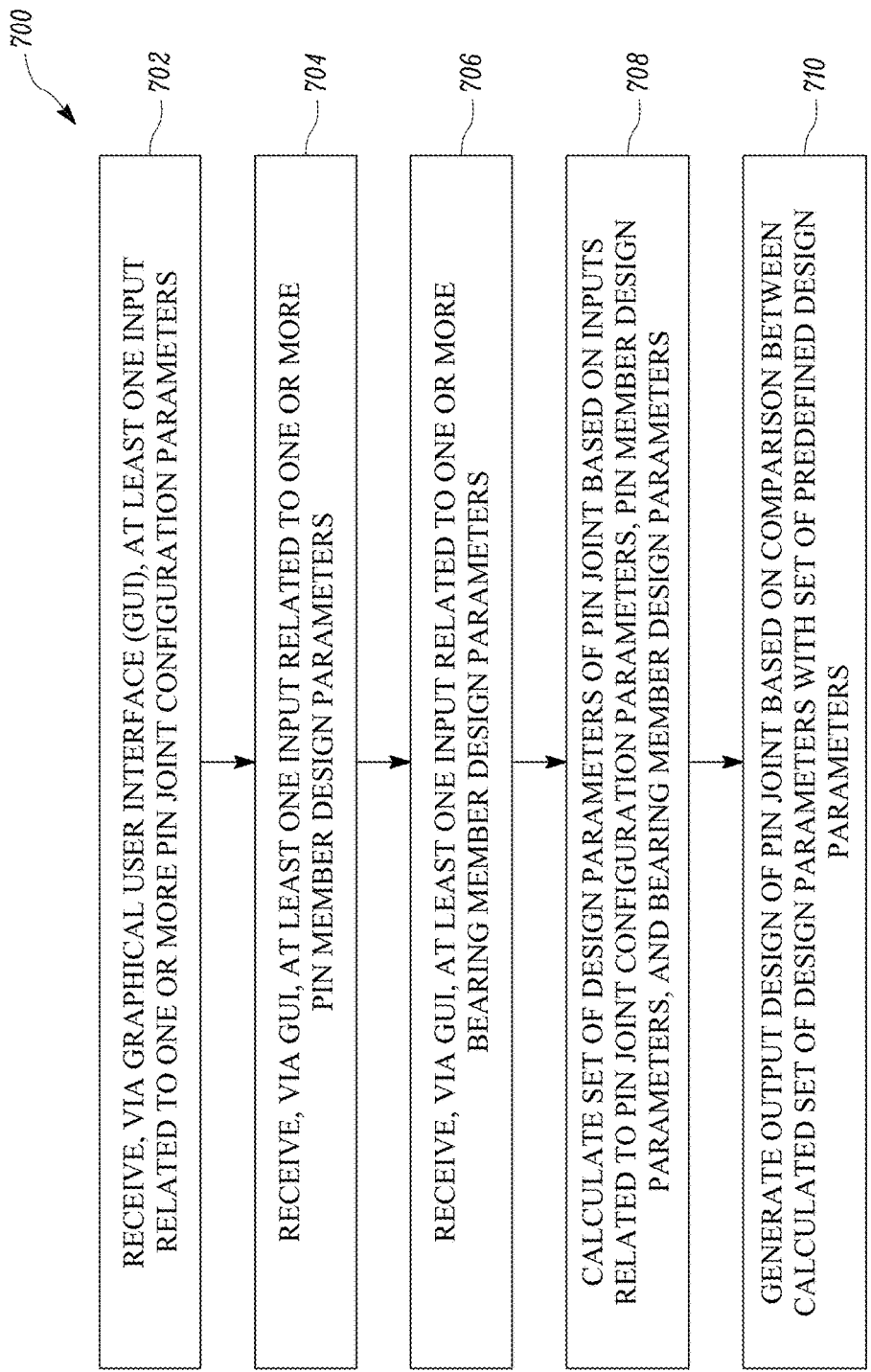
FIG. 12 is a flowchart of a method for designing a pin joint, according to an embodiment of the present disclosure.

FIG. 12 illustrates a flowchart of a computer-implemented method 700 for designing a pin joint 102 having a bearing member 104 and a pin member 106, according to an embodiment of the preset disclosure. In an embodiment, the method 700 may be implemented via the system 100 described above.

At step 702, the method 700 includes receiving, via the GUI 110, at least one input related to one or more pin joint configuration parameters. The pin joint configuration parameters may include the loading condition of the pin joint 102, and the coefficient of friction between the pin member 106 and the bearing member 104. In the illustrated embodiment, the set of control elements 207 may allow the user to provide inputs corresponding to the pin joint configuration parameters. Further, the processing device 120 may be configured to receive the pin joint configuration parameters via the set of control elements 207 of the process tab 206.

At step 704, the method 700 includes receiving, via the GUI 110, at least one input related to one or more pin member design parameters. The pin member design parameters may include the dimensional specification of the pin member, the material specification of the pin member 106, and the heat treatment specification of the pin member 106. In the illustrated embodiment, the control elements 210C, 210D, 210E, 210F, 210G of the process tab 210 may allow the user to provide inputs corresponding to the dimensional specification of the pin member 106. Further, the control elements 210H, 210I may allow the user to provide inputs related to the material specification of the pin member 106, and the heat treatment specification of the pin member 106, respectively. Furthermore, the processing device 120 may be configured to receive the pin member design parameters upon receiving the user inputs via the control elements of the process tab 210.

At step 706, the method 700 includes receiving, via the GUI 110, at least one input related to one or more bearing member design parameters. The bearing member design parameters may include a dimensional specification of the bearing member 104, and a material specification of the bearing member 104. In the illustrated embodiment, the processing device 120 may display or navigate to a process tab associated with the bearing member design parameters upon receiving instructions via at least one of the navigation buttons 212, 216, 220. For example, upon clicking the navigation button 204, the processing device 120 may display or navigate to the process tab 214 (see FIG. 4) of the GUI 110. The control elements of the process tabs 214, 218, 222 may allow the user to provide inputs that is indicative of the variables associated with the dimensional specification of the bearing member 104, and a material specification of the bearing member 104. Further, the processing device 120 may be configured to receive the user input via the control elements of the process tabs 214, 218, 222.

At step 708, the method 700 may include calculating a set of design parameters of the pin joint 102 based on the inputs related to the pin joint configuration parameters, the pin member design parameters, and the bearing member design parameters. In an example, the processing device 120 may be configured to perform a fatigue analysis to calculate the set of design parameters. At step 708, the method may also include displaying, via the GUI 110, the calculated set of design parameters. Upon calculating the set of design parameters, the processing device 120 may also be configured to auto-fill the table 226 of the process tab 224 for display to the user on the GUI 110. At step 708, the method 700 may also include comparing the calculated set of design parameters with the set of predefined design parameter. The processing device 120 may also be configured to retrieve the set of predefined parameters and compare a design parameter of the set of design parameters with a corresponding pre-defined design parameter. The processing device 120 may also be configured to generate the warning signal if a design parameter of the set of design parameters does not comply with a corresponding predefined design parameter.

At step 708, the method 700 may further include suggesting, via the GUI 110, a change in one or more design parameters of the set of design parameters based on the comparison between the calculated set of design parameters with the set of predefined design parameters. Referring to FIG. 10, as the user clicks the color markings 232, the processing device 120 may display the dialogue box 234 suggesting a change in a value of a design parameter in order to meet the design criteria of the pin joint 102, At step 710, the method 700 includes generating an output design of the pin joint 102 based on the comparison between the calculated set of design parameters with the set of predefined design parameters. At step 710, the method 700 may also include receiving, via the GUI, a user input indicative of the output parameter. The process tab 236 allows the user to provide inputs indicative of one or more output parameters. In an embodiment, the output parameters include, but not limited to, file path, a design control, a pin retention, a paint specification, simple flag pin assembly parameters, and multiple pin options. At step 710, the method 700 may also include generating the output design of the pin joint 102 based on the output parameter. In the illustrated embodiment, the control elements of the process tab 236 may allow the user to provide inputs indicative of the output parameters. The processing device 120 may be configured to receive the output parameters and generate the output design in various formats such as an excel spreadsheet, a 2D model, a 3D model, etc. In an example, the processing device 120 may also be configured to display the output design using a computer aided design software.

In an embodiment, at step 710, the method 700 may also include comparing the output design of the pin joint 102 with the plurality of pin joint designs stored in a library of existing pin joints. At step 710, the method 700 may further include suggesting a pin joint from the library of existing pin joints based on comparison between the output design and the plurality of pin joint designs of the library of existing pin joints. For example, if a pin joint of existing pin joints may be defined based on the calculated set of design parameters, the processing device 120 may generate the output design similar to the pin joint of existing pin joints.

The system 100 and the method 700 of the present disclosure have applicability for use and implementation in designing a pin joint 102. With such implementation, a pin joint 102 may be designed by taking into account various parameters, thereby accurately determining the total cost of the casting process. Additionally, with use of the system 100 and the method 700, the output design may be generated according to various scenarios and types of customers. For example, the system 100 and the method 700 may be used to selectively design at least one of a pin member 106 for a pin joint 102, a bearing member 104 for a pin joint 102, and a pin joint 102. The system 100 and the method 700 may also allow providing the output design in various formats. Such output designs may be stored in the pin joint database 130 in order to retrieve and modify later. Two or more such output designs may also be retrieved for designing a new pin joint. Also, the processing device 120 may be configured to select a saved output design of the pin joint 102 for displaying to the user, via GUI 110. Moreover, the processing device 120 may also be configured to compare the output design of the pin joint 102 with a plurality of pin joint designs already stored in the library of existing pin joints. The processing device 120 may also suggest a pin joint from the library of existing pin joints based on comparison between the output design and the plurality of pin joint designs of the library of existing pin joints. For example, if a pin joint of existing pin joints has the calculated set of design parameters, the processing device 120 may generate the output design similar to the pin joint of existing pin joints While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

What is claimed is:

1. A method comprising:
  receiving, via a Graphical User Interface (GUI), at least one input related to one or more pin joint configuration parameters;
  receiving, via the GUI, at least one input related to one or more pin member design parameters;
  receiving, via the GUI, at least one input related to one or more bearing member design parameters;
  calculating a set of design parameters of a pin joint based on the at least one input related to the one or more pin joint configuration parameters, the at least one input related to the one or more pin member design parameters, and the at least one input related to the one or more bearing member design parameters;
  comparing the set of design parameters with a set of predefined design parameters;
  providing, via the GUI and based on comparing the set of design parameters with the set of predefined design parameters, a color marking that indicates a level of acceptability of a design parameter of the set of design parameters;
  identifying a selection of the color marking;
  providing, via the GUI and based on the selection of the color marking, a dialogue box that includes information suggesting a change in a value of the design parameter of the set of design parameters;
  generating an output design of the pin joint based on comparing the set of design parameters with the set of predefined design parameters;
  comparing the output design of the pin joint with a plurality of pin joint designs stored in a library of existing pin joints; and
  suggesting a pin joint, from the library of existing pin joints, based on comparing the output design of the pin joint with the plurality of pin joint designs.

2. The method of claim 1, further comprising:
provinding, via the GUI, information identifying the calculated set of design parameters.

3. The method of claim 1, wherein the one or more pin joint configuration parameters comprise at least one of:
   a loading condition of the pin joint, or
   a coefficient of friction between a pin member, of the pin joint, and a bearing member of the pin joint.

4. The method of claim 1, wherein the one or more pin member design parameters comprise:
   a dimensional specification of a pin member of the pin joint,
   a material specification of the pin member, and
   a heat treatment specification of the pin member.

5. The method of claim 1, wherein the one or more bearing member design parameters comprise:
   a dimensional specification of a bearing member of the pin joint, and
   a material specification of the bearing member.

6. The method of claim 1, wherein the set of predefined design parameters is obtained from a pin joint database.

7. The method of claim 1, further comprising:
   receiving, via the GUI, a user input indicative of an output parameter,
   wherein the output design of the pin joint is generated further based on the output parameter.

8. A system comprising:
a memory; and
at least one processor configured to:
   receive, via a Graphical User Interface (GUI), at least one input related to one or more pin joint configuration parameters;
   receive, via the GUI, at least one input related to one or more pin member design parameters;
   receive, via the GUI, at least one input related to one or more bearing member design parameters;
   calculate a set of design parameters of a pin joint based on the at least one input related to the one or more pin joint configuration parameters, the at least one input related to the one or more pin member design parameters, and the at least one input related to the one or more bearing member design parameters;
   compare the set of design parameters with a set of predefined design parameters;
   provide, via the GUI and based on comparing the set of design parameters with the set of predefined design parameters, a color marking that indicates a level of acceptability of a design parameter of the set of design parameters;
   identify a selection of the color marking;
   provide, via the GUI and based on the selection of the color marking, a dialogue box that includes information suggesting a change in a value of the design parameter of the set of design parameters;
   generate an output design of the pin joint based on comparing the set of design parameters with the set of predefined design parameters;
   compare the output design of the pin joint with a plurality of pin joint designs; and
   suggest a pin joint from the plurality of pin joint designs, based on comparing the output design of the pin joint with the plurality of pin joint designs.

9. The system of claim 8, wherein the at least one processor is configured to:
   provide, via the GUI, information identifying the set of design parameters.

10. The system of claim 8, wherein the one or more pin joint configuration parameters comprise at least one of:
    a loading condition of the pin joint, and
    a coefficient of friction between a pin member, of the pin joint, and a bearing member of the pin joint.

11. The system of claim 8, wherein the one or more pin member design parameters comprise:
    a dimensional specification of a pin member of the pin joint,
    a material specification of the pin member, and
    a heat treatment specification of the pin member.

12. The system of claim 8, wherein the one or more bearing member design parameters comprise:
    a dimensional specification of a bearing member of the pin joint, and
    a material specification of the bearing member.

13. The system of claim 8, wherein the set of predefined design parameters is obtained from a pin joint database of the system.

14. The system of claim 8,
    wherein the at least one processor is further configured to:
      receive, via the GUI, a user input indicative of an output parameter, and
    wherein the output design of the pin joint is generated further based on the output parameter.

15. A non-transitory computer-readable storage device storing instructions, the instructions causing comprising:
    one or more instructions that, when executed by a computer, cause the computer to:
      receive, via a Graphical User Interface (GUI), at least one input related to one or more pin joint configuration parameters;
      receive, via the GUI, at least one input related to one or more pin member design parameters;
      receive, via the GUI, at least one input related to one or more bearing member design parameters;
      calculate a set of design parameters of a pin joint based on the at least one input related to the one or more pin joint configuration parameters, the at least one input related to the one or more pin member design parameters, and the at least one input related to the one or more bearing member design parameters;
      compare the set of design parameters with a set of predefined design parameters;
      provide, via the GUI and based on comparing the set of design parameters with the set of predefined design parameters, a color marking that indicates a level of acceptability of a design parameter of the set of design parameters;
      identify a selection of the color marking;
      provide, via the GUI and based on the selection of the color marking, a dialogue box that includes information suggesting a change in a value of the design parameter of the set of design parameters;
      generate an output design of the pin joint based on comparing the set of design parameters with the set of predefined design parameters;
      compare the output design of the pin joint with a plurality of pin joint designs stored in a library of existing pin joints; and
      suggest a pin joint from the library of existing pin joints based on comparison between the output design and the plurality of pin joint designs of the library of existing pin joints.

16. The non-transitory computer-readable storage device of claim 15, wherein the one or more instructions further cause the computer to:

provide, via the GUI, information identifying the set of design parameters.

17. The non-transitory computer-readable storage device of claim 15,
wherein the one or more instructions further cause the computer to:
receive, via the GUI, a user input indicative of an output parameter, and
wherein the output design of the pin joint is generated further based on the output parameter.

18. The non-transitory computer-readable storage device of claim 17, wherein the output parameter includes a file path.

19. The non-transitory computer-readable storage device of claim 15, wherein the at least one input related to one or more bearing member design parameters is received based on a selection of a type of material of a bearing member, of the pin joint, from a drop down menu.

20. The non-transitory computer-readable storage device of claim 15, wherein the one or more instructions further cause the computer to:
auto-fill, after calculating the set of design parameters, values of the set of design parameters in a user interface element displayed on the GUI.

* * * * *